(12) United States Patent
Guala

(10) Patent No.: US 9,345,871 B2
(45) Date of Patent: May 24, 2016

(54) INJECTION SITE FOR TUBULAR MEDICAL CONNECTORS

(75) Inventor: Gianni Guala, Turin (IT)

(73) Assignee: INDUSTRIE BORLA S.P.A., Moncalieri (Torino) (IT)

( * ) Notice: Subject to any disclaimer, the term of this patent is extended or adjusted under 35 U.S.C. 154(b) by 105 days.

(21) Appl. No.: 14/123,461

(22) PCT Filed: May 31, 2012

(86) PCT No.: PCT/IB2012/052736
§ 371 (c)(1),
(2), (4) Date: Feb. 24, 2014

(87) PCT Pub. No.: WO2012/164514
PCT Pub. Date: Dec. 6, 2012

(65) Prior Publication Data
US 2014/0200557 A1    Jul. 17, 2014

(30) Foreign Application Priority Data

Jun. 1, 2011   (IT) .............................. TO2011A0481

(51) Int. Cl.
*A61M 39/04*     (2006.01)
*A61M 39/26*     (2006.01)
*A61M 39/00*     (2006.01)

(52) U.S. Cl.
CPC .............. *A61M 39/04* (2013.01); *A61M 39/26* (2013.01); *A61M 2039/0063* (2013.01)

(58) Field of Classification Search
CPC ................... A61M 39/04; A61M 2039/0063; A61M 2039/0072
See application file for complete search history.

(56) References Cited

U.S. PATENT DOCUMENTS 2,546,672 A  *  3/1951  Le Clair .................. F16N 21/02
                                                    184/105.3
4,294,249 A  *  10/1981  Sheehan et al. .................. 604/86
(Continued)

FOREIGN PATENT DOCUMENTS

CN       101732793 A    6/2010
WO       WO 89/00867     2/1989
(Continued)

OTHER PUBLICATIONS

International Search Report and Written Opinion of the International Searching Authority, mailed on Nov. 26, 2012, for corresponding PCT International Application No. PCT/IB2012/052736 filed on May 31, 2012, and completed on Nov. 15, 2012.
(Continued)

*Primary Examiner* — Andrew Gilbert
(74) *Attorney, Agent, or Firm* — Heslin Rothenberg Farley & Mesiti P.C.; Victor A. Cardona, Esq.

(57) ABSTRACT

An injection site for tubular medical connectors, includes a perforable body inserted in a seat of a connector delimited by an annular wall having a retention edge turned in against the outer end of the perforable body. The outer end is formed with a peripheral annular step and with an exposed portion with reduced cross section projecting axially. The peripheral step is defined by an annular groove having a shape complementary to that of the turned-in retention edge of the connector, and the portion with reduced cross section of the perforable body connects up to the groove through an annular surface projecting radially above at least part of the turned-in retention edge and resting against it.

7 Claims, 2 Drawing Sheets

(56) References Cited

U.S. PATENT DOCUMENTS

| | | | | |
|---|---|---|---|---|
| 4,809,679 | A * | 3/1989 | Shimonaka | A61B 1/00137 600/154 |
| 4,874,369 | A * | 10/1989 | Kulle et al. | 604/86 |
| 5,070,905 | A * | 12/1991 | Paradis | 137/606 |
| 5,100,394 | A * | 3/1992 | Dudar et al. | 604/537 |
| 5,115,950 | A * | 5/1992 | Rohr | 222/490 |
| 5,300,034 | A * | 4/1994 | Behnke et al. | 604/167.02 |
| 5,400,500 | A | 3/1995 | Behnke et al. | |
| 5,403,293 | A * | 4/1995 | Grabenkort | A61J 1/1406 604/256 |
| 5,603,706 | A * | 2/1997 | Wyatt | A61M 39/04 137/223 |
| 5,632,735 | A * | 5/1997 | Wyatt | A61M 39/04 285/309 |
| 5,797,897 | A * | 8/1998 | Jepson | A61J 1/2089 604/239 |
| 6,171,287 | B1 * | 1/2001 | Lynn | A61M 39/02 251/149 |
| 8,187,162 | B2 * | 5/2012 | Coe et al. | 600/33 |
| 8,211,089 | B2 * | 7/2012 | Winsor | A61M 39/045 604/284 |
| 2003/0109853 | A1 | 6/2003 | Harding et al. | |
| 2007/0233018 | A1 * | 10/2007 | Bizup et al. | 604/288.01 |
| 2008/0103487 | A1 * | 5/2008 | Miyasaka | 604/537 |
| 2009/0228028 | A1 * | 9/2009 | Coe et al. | 606/157 |

FOREIGN PATENT DOCUMENTS

| | | |
|---|---|---|
| WO | WO 90/11103 | 10/1990 |
| WO | WO 92/19293 | 11/1992 |
| WO | WO 2010/069361 A1 | 6/2010 |
| WO | WO 2010/073643 A1 | 7/2010 |

OTHER PUBLICATIONS

Corresponding Chinese Office Action dated Mar. 30, 2015, for Chinese Application No. 201280026971.2.

* cited by examiner

INJECTION SITE FOR TUBULAR MEDICAL CONNECTORS

CROSS REFERENCE TO RELATED APPLICATIONS

This application is a national stage of PCT International Application No. PCT/IB2012/052736, filed on May 31, 2012, and published in English on Dec. 6, 2012, as WO 2012/164514 A2, and which claims priority to Italian Patent Application No. TO2011A000481 filed on Jun. 1, 2011, the entire disclosures of which are incorporated herein by reference.

FIELD OF THE INVENTION

The present invention relates to tubular medical connectors, typically for infusion or transfusion lines, equipped with an injection site for introduction of fluid substances into the connector.

Traditionally in connectors of this sort, which are normally made of moulded plastic material, the injection site is constituted by a perforable body made of elastomeric material or thermoplastic rubber inserted into a seat of the connector delimited by an annular end wall having a retention edge. Following upon insertion of the perforable body into said seat, the end edge of the wall of the connector is turned in, for example by means of hot or cold deformation or else via ultrasound, so as to block the perforable body stably in its seat.

PRIOR ART

Currently, the perforable body is shaped like a generally cylindrical wafer with constant cross section so that the turned-in retention edge of the wall of the corresponding seat is set in frontal contact against the outer end of said body. In this way, a perimetral discontinuity is determined along the resting area of the turned-in retention edge that not only renders disinfection or sterilization of the surface of said end prior to introduction of the needle problematical, but can also constitute a trap for impurities.

From the documents Nos. WO-2010/069361, WO-90/11103, U.S. Pat. No. 5,400,500 and WO-89/00867 injection sites of the type defined above are known, in which the outer end of the perforable body is formed with a peripheral annular step for engagement of the turned-in retention edge of the wall of the connector, and with a portion with reduced cross section projecting axially beyond the annular step.

This solution makes it easier to disinfect or sterilize the exposed end of the perforable body prior to introduction of the needle thanks to the more immediate accessibility from outside of the portion projecting axially beyond the annular step, but entails, however, again the drawback that possible impurities can deposit and get stuck in the annular space comprised between the surface of the turned-in retention edge of the wall of the connector and the side wall facing it of the axially projecting portion with reduced cross section of the perforable body.

SUMMARY OF THE INVENTION

The object of the present invention is hence to overcome said drawback in an effective and at the same time simple and economically advantageous way.

According to the invention this object is achieved thanks to the fact that the aforesaid step is defined by an annular groove having a shape complementary to that of said turned-in retention edge of the wall of the connector and to the fact that the portion with reduced cross section of the perforable body connects up to said groove through an annular surface projecting radially above at least part of said turned-in retention edge and resting thereagainst.

Thanks to this arrangement, the turned-in retention edge of the wall of the connector impinges laterally instead of frontally upon the perforable body and is at least partially overlaid and hence covered by the radially projecting annular surface of said perforable body, the exposed surface of which remains immediately accessible from outside so that it can effectively be disinfected prior to insertion of the needle.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

Figure 1:
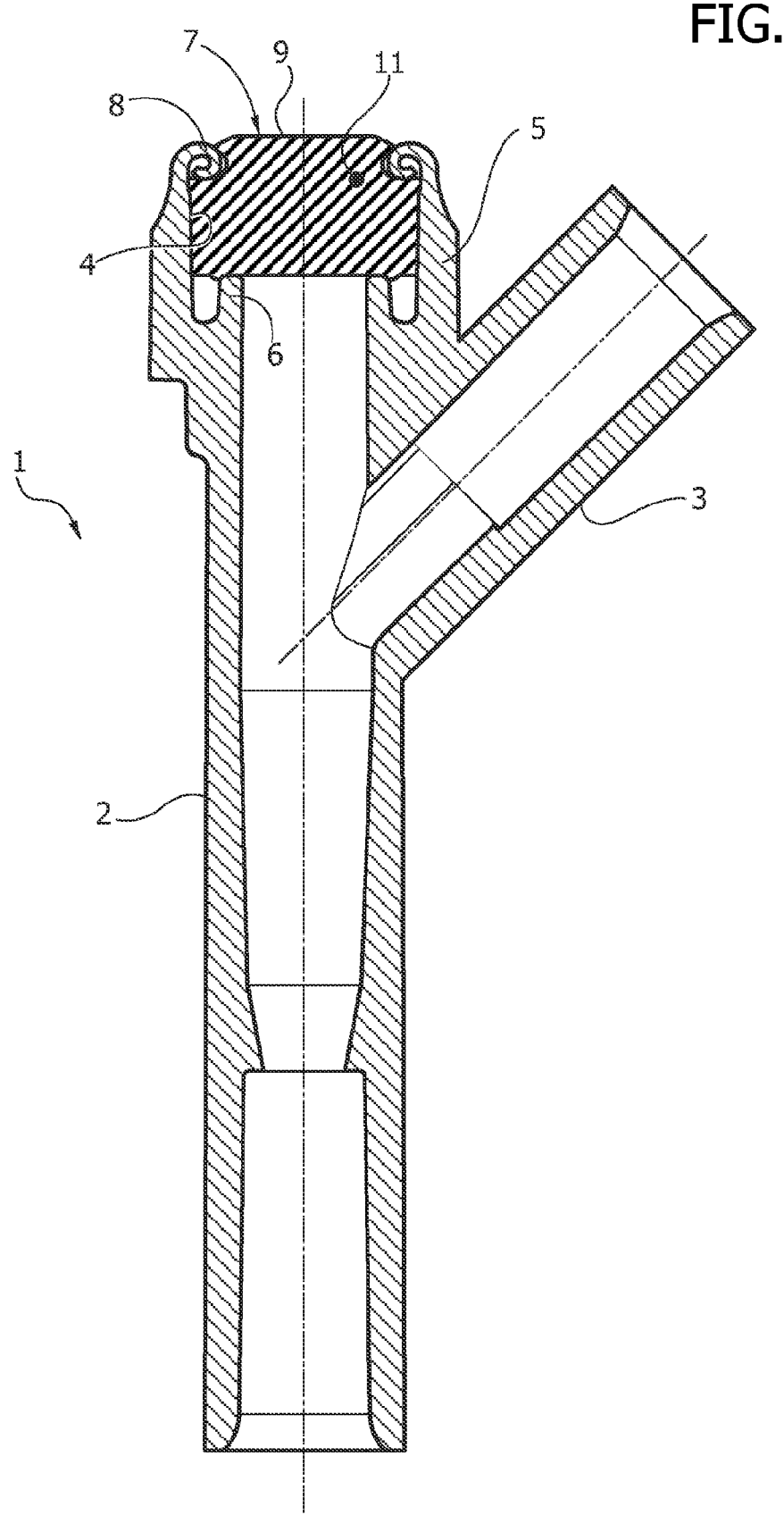
FIG. 1 is a schematic view in axial section of a medical connector provided with an injection site according to the invention.

With reference to the drawings, designated by 1 is a tubular connector for medical lines, which, in the case of the example illustrated, has a Y-shaped configuration with a main duct 2 and a secondary duct 3 with mutually communicating convergent axes.

The end of the main duct 2 adjacent to the secondary duct 3 has a seat 4 delimited laterally by an annular wall 5 and internally by an axial annular rest 6.

Housed in the seat 4 is a body 7 shaped like a wafer, typically made of elastomeric material or thermoplastic rubber, which can be perforated with a needle. The body 7 hence defines an injection site or needle point for introduction into the connector 1 of a medical fluid or the like.

The body 7, enclosed in the wall 5, on one side impinges axially on the annular rest 6 and on the opposite side is blocked, at its end 9 exposed towards the outside of the tubular connector 1, by an annular retention edge 8 of the wall 5. Since normally the connector 2 is made of moulded thermoplastic material, the retention edge 8 is bent i.e. turned in by means of hot or cold deformation or else via ultrasound so as to assume substantially the conformation represented in FIG. 1, i.e., a curled shape rounded and closed on itself for an angular amplitude substantially greater than 180°.

According to the peculiar characteristic of the invention, the retention edge 8 is turned in not frontally against the surface of the end 9 of the perforable body 7, as is instead the case of the known art, but at the side thereof and is moreover at least partially covered and protected at the top by the perforable body 7.

Figure 2:
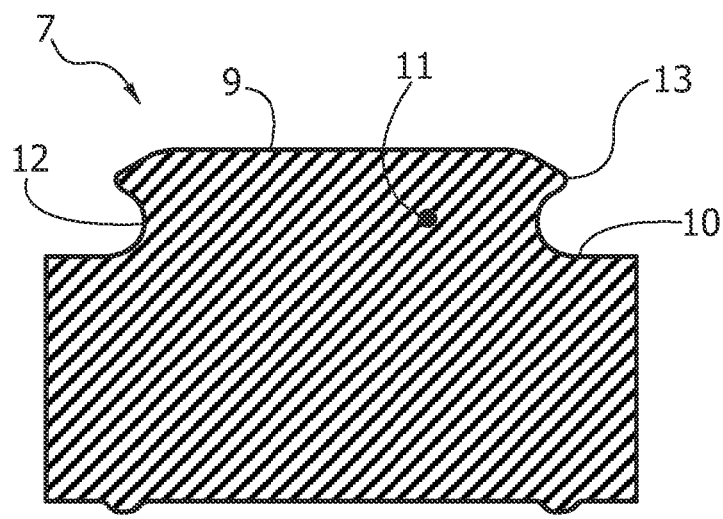
FIG. 2 is the view in axial section at an enlarged scale of the perforable body of the injection site of FIG. 1.
Figure 3:
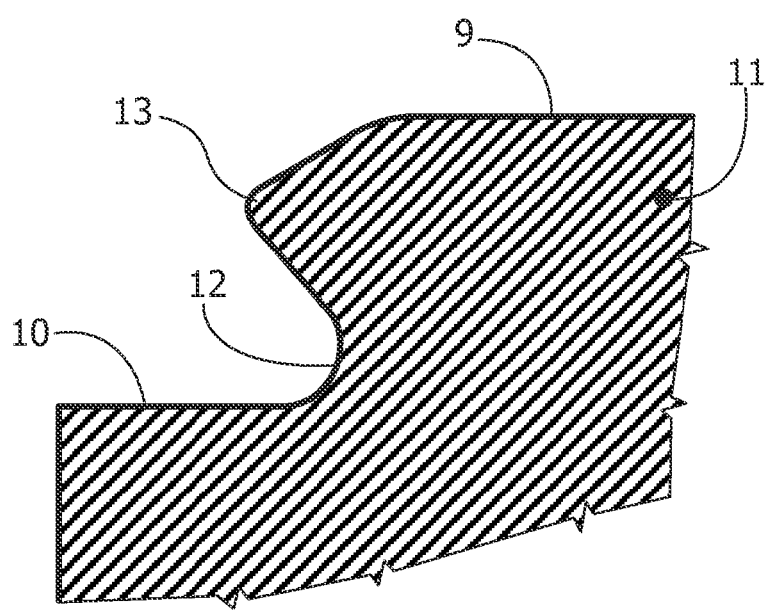
FIG. 3 shows a detail of FIG. 2 at a further enlarged scale.

More in particular, and as is illustrated in detail in FIGS. 2 and 3, the perforable body 7 is formed, in the proximity of its exposed end 9, with a peripheral annular step 10 that radiuses with a portion with reduced cross section 11, which defines the exposed surface of the end 9 of the perforable body 7. As is even more clearly visible in FIG. 3, the step 10 is defined by a peripheral groove with rounded wall 12, having a shape complementary to that of the turned-in retention edge 8, which connects up with the portion with reduced cross section 11 through an annular lip 13 with tapered profile, projecting radially outwards above the step 10.

To return to FIG. 1, the retention edge 8 of the wall 5 is turned in against the step 10, within the annular groove 12, and the lip 13 of the portion with reduced cross section 11 rests at the top against it.

In this way, the surface of the exposed end 9 of the perforable body 7 axially projects beyond the retention edge 8, facilitating the necessary operations of disinfection or sterilization, in use of the connector 1, prior to perforation of the body 7 by a needle. At the same time, engagement of the retention edge 8 in the groove 12 and its at least partial covering by the radially projecting annular lip 13 effectively prevents introduction of impurities between said retention edge 8 and the perforable body 7.

Of course, the details of construction and the embodiments may vary widely with respect to what is described and illustrated herein, without thereby departing from the scope of the present invention as defined in the ensuing claims. Thus, even though the invention has been described with reference to a Y-shaped tubular connector, it is equally advantageously applicable to an injection site of medical connectors of any kind.

The invention claimed is:

1. An injection site for tubular medical connectors, comprising:
   a non-slitted perforable body configured for perforation by a needle during use, said perforable body received in a seat of a connector delimited by an annular wall having a turned-in retention edge turned in against an outer end of said perforable body;
   said perforable body having a first end opposite said outer end and a side wall lateral to said first end;
   said outer end of the perforable body having a peripheral annular step for engagement of said turned-in retention edge of said annular wall of the connector;
   said peripheral annular step extending inwardly from said side wall;
   said peripheral annular step bounded by an annular groove having a rounded wall complementary to that of said turned-in retention edge; and
   said outer end having an exposed portion with a reduced cross section projecting axially beyond said peripheral annular step in an axial direction parallel to a longitudinal axis of said connector and away from said seat, said exposed portion projecting in said axial direction beyond said turned-in retention edge;
   said annular groove extending from said peripheral annular step to connect to a lip of said exposed portion;
   said lip projecting radially above said turned-in retention edge such that an outermost radial extent of said lip is radially inward of an outermost radial extent of said peripheral annular step.

2. The injection site according to claim 1, wherein said lip has a tapered profile.

3. The injection site according to claim 1, wherein said turned-in retention edge of said annular wall of the connector and said annular groove of the outer end of the perforable body have a rounded shape.

4. The injection site according to claim 2, wherein said turned-in retention edge of said annular wall of the connector and said annular groove of the outer end of the perforable body have a rounded shape.

5. The injection site according to claim 1 wherein said outer end has a smaller diameter than a remaining portion of said perforable body extending away from said outer end toward an annular rest of said seat.

6. The injection site according to claim 1 wherein said turned-in retention edge extends radially inward from said annular wall and has an arc shaped inner surface for contacting said peripheral annular groove, said turned-in retention edge having a terminal end located radially outward of said exposed portion.

7. The injection site according to claim 1 wherein said exposed portion comprises a planar portion and said lip tapers radially outwardly from said planar portion.

* * * * *